United States Patent [19]

Wehner et al.

[11] Patent Number: 4,752,570

[45] Date of Patent: Jun. 21, 1988

[54] PROCESS FOR THE DETERMINATION OF PEROXIDASE

[75] Inventors: Rainer Wehner, Gauting; Helmut Lenz, Tutzing, both of Fed. Rep. of Germany

[73] Assignee: Boehringer Mannheim GmbH, Mannheim-Waldhof, Fed. Rep. of Germany

[21] Appl. No.: 774,044

[22] Filed: Sep. 9, 1985

[30] Foreign Application Priority Data

Oct. 22, 1984 [DE] Fed. Rep. of Germany ..... 34386831

[51] Int. Cl.$^4$ ............ G01N 33/535; C12Q 1/30; C12Q 1/28; C12N 9/99
[52] U.S. Cl. ............................. 435/7; 435/27; 435/28; 435/184
[58] Field of Search ............ 435/27, 28, 184, 810, 435/7; 424/53

[56] References Cited

U.S. PATENT DOCUMENTS 4,155,868  5/1979  Kaplan et al. .................. 424/53
4,615,972  10/1986  Gallacher ........................ 435/4

FOREIGN PATENT DOCUMENTS 169498  9/1984  Japan .

OTHER PUBLICATIONS

Chemical Abstracts, Band 99, Nr. 5, 01, Aug. 1983, "Adaptation of the Ngo-Lenhoff Peroxidase Assay for Solid Phase ELISA".
Feinstein, "Perborate As Substrate In a New Assay of Catalase", pp. 1197-1201 (1949).
Van Vunakis, et al., Meth. Enzymol. 70: 432 (1980).
Bovaird, et al., Clin. Chem. 28(12): 2423-2426 (1982).
Rook, Lepr. Rev. 52: 281-285 (1981).
Gallati, Clin. Chem. Clin. Biochem. 17: 1-7 (1979).
Al-Kaissi, et al., J. Immunol. Meth. 58: 127-132 (1983).
Chance, B. et al, (1964) Methods in Enzymology vol. 2, pp. 764-775.
Lenhoff et al, (1964) Methods in Enzymology vol. 2, pp. 758-764.
Singh et al, (1980) Anolytica Chimica Acta, vol. 115, pp. 401-405.

Primary Examiner—Esther M. Kepplinger
Assistant Examiner—William J. Herald
Attorney, Agent, or Firm—Felfe & Lynch

[57] ABSTRACT

The present invention provides a process for the determination of peroxidase by the addition of a peroxide and of a chromogen and measurement of the color resulting from the oxidation of the chromogen, the color formation being stopped after a definite time by the addition of a stop agent, wherein catalase is used as stop agent.

9 Claims, No Drawings

PROCESS FOR THE DETERMINATION OF PEROXIDASE

The present invention is concerned with a process for the determination of peroxidase.

The determination of peroxidase is of importance in various technical fields. In recent years, the increasing use of peroxidase as marking enzyme in the scope of the so-called enzyme immune determination (EIA), which has supplanted to a considerable extent the previously usual radioimmune determination (RIA), has thereby achieved great importance. The enzyme immune determination of haptens, antigens and antibodies is an extraordinarily sensitive process which, therefore also places correspondingly high demands on the exactitude of the determination of the marking enzymes thereby used. In the case of the very frequent use of peroxidase as marking enzyme, the enzyme activity determination frequently takes place according to the fixed time method by extinction measurement. In principle, the process depends upon the face that peroxidase (POD) oxidises an appropriate chromogen in the presence of an peroxide with the formation of a colour, the speed of the colour formation corresponding to the activity or amount of the POD. In the case of the fixed time method, after a definite reaction time after addition of the substrate (usually 30 to 60 minutes), the colour formed is measured against a blank. Since, at this point of time, the colour reaction is, in general, not yet concluded, it must be ensured that the same incubation times are maintained for all standards and samples. This requires that not only the substrate addition but also the extinction measurement must be carried out in an exactly fixed space of time of, as a rule, 10 to 15 seconds between the individual test tubes. This disadvantage, which makes the handling difficult, can be avoided by using a stop agent for the reaction.

In the above-mentioned connection, it is already known from U.S. Pat. No. 4,234,680 to use an alkali metal bisulphite as stop agent. However, this agent has the disadvantage, as reducing agent, of attacking the colour formed in the case of the oxidation reaction and of reducing it with decolorisation thereof. This applies especially for 2,2'-azino-di-(3-ethylbenzthiazoline-6-sulphonic acid) salts, usually the diammonium salt (ABTS)®, which is particularly suitable as a chromogen for POD determinations, in the case of which a bleaching of the colour takes place within a short period of time.

Another stop agent for the POD reaction is formaldehyde. However, the stability of the colour solution mixed with the agent is here unsatisfactory. There is also to be added the troublesome smell and the potential danger to health caused by formaldehyde.

Another known stop agent for POD is oxalic acid. However, this agent results in an impairment of the precision of the determination. This applies especially when solid bodies (e.g. tubes or spheres) coated with antibodies are used for the enzyme immune determination in the case of which, in general, the POD bound to the wall after separation of the liquid phase from the solid phase is determined in the usual way. In the case of the addition of oxalic acid, such protein bound to the solid phase can, however, be loosened therefrom and/or denatured.

A further known stop agent is sodium azide. Here, too, there is a danger of a bleaching of the colour. Furthermore, there is a danger of explosion in combination with heavy metal salts.

Finally, surface-active agents, such as secondary alkyl sulphate or dodecyl hydrogen sulphate, have been suggested as stop agents. However, they are not able fully to suppress the colour formation.

Therefore, it is an object of the present invention to overcome the disadvantages of these known stop agents and to provide a process for the determination of peroxidase in the case of which a stopping of the colour formation at a definite, predetermined point of time is possible, which is immediately effective and which does not result in a disadvantageous change of the colour present at the point of time of the addition of the stop agent.

Thus, according to the present invention, there is provided a process for the determination of peroxidase by the addition of a peroxide and of a chromogen and kinetic measurement of the colour resulting from the oxidation of the chromogen, the colour formation being stopped after a definite period of time by the addition of a stop agent, wherein catalase is used as stop agent.

The process according to the present invention has an immediate stop action of the colour formation but does not subsequently change this so that it is possible, within several hours after the stopping, to carry out a measurement of the colour formed at any desired point of time.

The process according to the present invention can be used for all chromogens useful for carrying out POD determinations. Typical examples of appropriate chromogens include 2,2'-azino-di-(3-ethylbenzthiazoline-6-sulphonic acid) diammonium salt (ABTS)®, o-phenylenediamine, p-phenylenediamine, m-aminosalicylic acid, dianisidine, p-aminobenzoic acid, aniline, 4-aminoantipyrine and the like. These chromogens are well known for POD determinations and do not here require any further explanation. ABTS® is preferably used. o-Phenylenediamine and 4-aminoantipyrine are also preferred.

The amount of catalase which is added in carrying out the process according to the present invention is not critical. However, it must be in excess with regard to the possible POD activity present. In the scope of an enzyme immune determination, the added amount of POD, of which only a part must then be determined, is known. In the case of the determination of POD in other connections, in case of doubt, the order of magnitude of POD can be determined by a simple preliminary experiment and then the amount necessary for the achievement of an excess of catalase can be easily ascertained. In general, amounts of from 50 to 1000 U catalase per determination batch are used but, for certain cases, smaller amounts of catalase can also suffice or still larger amounts are desirable.

The process according to the present invention is also especially useful when the POD to be determined is present in immunologically or chemically bound form. This is, for example, the case when using POD in the form of conjugates, for example chemically bound to an antibody, an antibody fragment, an antigen, a globulin fraction or the like. The process according to the present invention can also be very useful in case where the POD is present immunologically fixed as such or via a ligand chemically bound with it, which can be connected to a solid phase. In the case of these embodimental forms of POD determinations, the requirements for a stop agent are especially critical since actions of the stop agent on the binding partner of the POD can easily result in falsifications of the results. Naturally, the process of the present invention is particularly useful for the determination of free, dissolved POD.

In the case of the process according to the present invention, the measurement of the colour formed can be carried out without disadvantageous influence on the precision of the determination within the course of several hours after the addition of the catalase. This is a considerable simplification and excludes various possibilities of error.

The following Examples are given for the purpose of illustrating the present invention:

EXAMPLE 1

Stopping of the colour formation reaction in the ABTS ® system

The Enzymun-Test ® TSH of Boehringer Mannheim GmbH (order No. 736082) is hereby used. This test contains POD, chemically bound in the form of antibody-POD conjugate which, during the immune reaction, is bound to the vessel wall of a sample tube made of plastic as well as ABTS ® as chromogen and sodium perborate as peroxide.

The test is carried out according to the manufacturer's instructions with a TSH standard (50 µU/ml.). Sample serum to be investigated is incubated for 60 minutes at pH 6.9 (phosphate buffer) in the same tube, then antibody-POD conjugate is added thereto and incubated for 60 minutes. Perborate and ABTS ® in phosphate-citrate buffer (pH 4.4) are then added thereto. The colour formation reaction

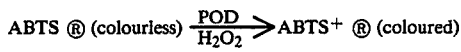

is stopped after 60 minutes by the addition of 0.1 ml. of a stop reagent consisting of
 250 U/ml. catalase
 50 mmol/l. acetate buffer, pH 5.5
 2% by weight Triton X-405 (non-ionic, surface-active agent).

Subsequently, the extinction of the solution is measured at 405 nm every 60 minutes for 3 hours. The following extinctions (referred to the addition of the solution (t=0, E=100%)) are thereby obtained:

TABLE I

| time (min.) | 0 | 60 | 120 | 180 |
|---|---|---|---|---|
| extinction | 100% | 99.8% | 100% | 98.5% |

EXAMPLE 2

Stopping of the colour formation reaction in the o-phenylenediamine system

Commercially-available CEA-EIA test (Abbot, order No. 586324) is used. This reagent contains POD chemically bound as antibody-POD conjugate which is bound during the immune reaction to synthetic resin spheres and o-phenylenediamine as substrate. The test is carried out, according to the manufacturer's instructions, with 2 CEA samples (concentration 1 or 5 ng/m/l CEA).

The oxidation (colour formation) of o-phenylenediamine with POD and hydrogen peroxide is stopped after 30 minutes by the addition of 2 ml. of a stop reagent according to Example 1 which, however, had been diluted with water in the ratio of 1:20 v/v. For the 2 samples, numbered in increasing concentration, there are obtained the following extinctions and referred to the point of time of stopping, t=0:

TABLE II

| sample | time = 0' | time = 90' |
|---|---|---|
| 1 | 100.0% | 100.0% |
| 2 | 100.0% | 103.1% |

EXAMPLE 3

Comparison of the stop action of catalase and formaldehyde

The reagents according to Example 1 are used. For comparison, instead of the stop agent of Example 1, there is used a 25% by weight solution of formaldehyde. In each case, the stopping of the colour formation reaction took place with 0.2 ml. of stop reagent. The following extinctions were thereby measured at 405 nm (referred to the point of time of the stopping t=0):

TABLE III

| Formaldehyde as stop reagent | | | | |
|---|---|---|---|---|
| time | 0' | 60' | 120' | 180' |
| extinction | 100% | 98.1% | 91.3% | 89% |
| Stop reagent according to Example 1 (catalase) | | | | |
| time | 0' | 60' | 120' | 180' |
| extinction | 100% | 98.8% | 99.8% | 100.1% |

EXAMPLE 4

Comparison of the precision in the case of using catalase and oxalic acid as stop reagent The reagents according to Example 1 are used. The experiment is carried out analogously to Example 1 but, instead of the there-described stop reagent, there is used 0.2 ml. of a 7% by weight oxalic acid solution. A comparison experiment with catalase is carried out according to Example 1. The stop action of oxalic acid can be seen from the following Table IV:

TABLE IV

| time | 0' | 60' | 120' | 180' |
|---|---|---|---|---|
| extinction | 100% | 112.6% | 117.0% | 114.0% |

The extinction of the solution is measured at 405 nm (point of time of the stopping t=0) for 10 different batches with catalase and oxalic acid. The results obtained are given in the following Table V:

TABLE V

| | 0' | 60' | 120' | 180' |
|---|---|---|---|---|
| VC with catalase | 1.1 | 0.7 | 1.5 | 2.7 |
| VC with oxalic acid | 2.0 | 3.5 | 6.0 | 8.5 |

It can be seen that the precision of the determination with oxalic acid as stop reagent is considerably impaired.

EXAMPLE 5

Stopping of the colour formation reaction in the ABTS ® system (non-wall-bound POD conjugate)

Solution 1: thyroxin-POD conjugate, activity: 0.6 mU/ml., dissolved in phosphate buffer (40 mM)

Solution 2: phosphate-citrate buffer, 100 mMol/l., hydrogen peroxide, 3 mMol/l. ABTS ®, 1.6 mMol/l.

Solution 3 (stop reagent): acetate buffer, 50 mMol/l. catalase, 250 U/ml. Triton X-405, 2%

8 μl. of solution 1 are added to 1 ml. of solution 2. The colour formation reaction:

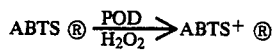

is stopped after 30 minutes by the addition of 100 μl. of solution 3 and the extinction measured at 405 nm immediately (T=0') and after 60 minutes. The results obtained are given in Table VI:

TABLE VI

|  | T = 0' | T = 60' |
|---|---|---|
| $E_{405}$ | 100% | 102% |

We claim:

1. Process for the determination of peroxidase comprising adding to a sample sodium perborate and a chromogen selected from the group consisting of o-phenylenediamine and a 2,2-azino-di-(3-ethylbenzthiazoline-6-sulphonic acid) salt and measuring a colour resulting from the oxidation of the chromogen, whereby said colour formation is stopped after a definite time by addition thereto of a catalase as a stop agent.

2. The process of claim 1, wherein immunologically bound peroxidase is determined.

3. The process of claim 1, wherein the chromogen is a 2,2'-azino-di-(3-ethylbenthiazolin-6-sulphonic acid) salt.

4. The process of claim 1 wherein the catalase is added in the form of a solution buffered to pH 5 to 7.

5. The process of claim 2 wherein the chromogen is a 2,2'-azino-di-(3-ethylbenzthiazolin-6-sulphonic acid) salt.

6. The process of claim 5 wherein the catalase is added in the form of a solution buffered to pH 5 to 7.

7. The process of claim 4 wherein the solution further contains a non-ionic wetting agent.

8. Process of claim 1, wherein chemically bound peroxidase is determined.

9. Process of claim 1, wherein the chromogen is o-phenylenediamine.

* * * * *